(12) United States Patent
Jo et al.

(10) Patent No.: US 12,377,165 B2
(45) Date of Patent: Aug. 5, 2025

(54) EXOSOME COMPRISING PHOTOCLEAVABLE PROTEIN, AND USE THEREOF

(71) Applicant: EXOSTEMTECH CO., LTD., Ansan-si (KR)

(72) Inventors: Dong Gyu Jo, Suwon-si (KR); Jihoon Han, Suwon-si (KR); Jaehoon Sul, Suwon-si (KR)

(73) Assignee: EXOSTEMTECH CO., LTD., Ansan-si (KR)

( * ) Notice: Subject to any disclaimer, the term of this patent is extended or adjusted under 35 U.S.C. 154(b) by 563 days.

(21) Appl. No.: 17/798,524

(22) PCT Filed: Feb. 8, 2021

(86) PCT No.: PCT/KR2021/001634
§ 371 (c)(1),
(2) Date: Aug. 9, 2022

(87) PCT Pub. No.: WO2021/162375
PCT Pub. Date: Aug. 19, 2021

(65) Prior Publication Data
US 2023/0211010 A1  Jul. 6, 2023

(30) Foreign Application Priority Data

Feb. 10, 2020  (KR) .................. 10-2020-0015696
Feb. 4, 2021  (KR) .................. 10-2021-0015837

(51) Int. Cl.
| | | |
|---|---|---|
| A61K 47/69 | (2017.01) | |
| A61K 9/1271 | (2025.01) | |
| A61K 9/50 | (2006.01) | |
| A61K 38/00 | (2006.01) | |
| A61K 41/00 | (2020.01) | |
| A61K 47/64 | (2017.01) | |
| C40B 30/06 | (2006.01) | |
| G01N 33/50 | (2006.01) | |

(52) U.S. Cl.
CPC ........ *A61K 47/6911* (2017.08); *A61K 9/1271* (2013.01); *A61K 47/6425* (2017.08); *C07K 2319/01* (2013.01); *C07K 2319/60* (2013.01)

(58) Field of Classification Search
None
See application file for complete search history.

(56) References Cited

U.S. PATENT DOCUMENTS

| | | |
|---|---|---|
| 2017/0190749 A1 | 7/2017 | Campbell |
| 2018/0117117 A1 | 5/2018 | Choi |
| 2019/0167810 A1 | 6/2019 | Hean |

FOREIGN PATENT DOCUMENTS

| | | |
|---|---|---|
| CN | 107446052 A | 12/2017 |
| KR | 10-2018-0036134 A | 4/2018 |
| KR | 10-2019-0011279 A | 2/2019 |
| WO | 2015/160690 A1 | 10/2015 |

OTHER PUBLICATIONS

Fadi M. Jradi et al., "Chemistry of Photosensitive Fluorophores for Single-Molecule Localization Microscopyscopy," ACS Chemical Biology, 2019.
Andrii A. Kaberniuk et al., "moxMaple3: a Photoswitchable Fluorescent Protein for PALM and Protein Highlighting In Oxidizing Cellular Environments," Scientific Reporters, 2018.
Renee Wei-Yan Chow, "The rise of photoresponsive protein technologies applications in vivo: a spotlight on zebrafish developmental and cell biology," F1000Research, 2017.
Turkowyd, Bartosz et al., "A General Mechanism of Photoconversion of Green-to-Red Fluorescent Proteins Based on Blue and Infrared Light Reduces Phototoxicity in Live-Cell Single-Molecule Imaging", Angewandte Chemie International Edition, 2017, vol. 56, pp. 11634-11639.
Ann L. McEvoy et al., "mMaple: A Photoconvertible Fluorescent Protein for Use in Multiple Imaging Modalities," Plos One, Dec. 11, 2012, p. e51314, vol. 7, No. 12, XP093122085.
Chunying Liu et al., "Design strategies and application progress of therapeutic exosomes," Theranostics, Jan. 1, 2019, pp. 1015-1028, vol. 9, No. 4, XP055698379.
Qinqin Cheng et al., "Expanding the toolbox of exosome-based modulators of cell functions," Biomaterials, Sep. 12, 2021, vol. 277, XP086797549.
Yuwei Huang et al., "Migrasome formation is mediated by assembly of micron-scale tetraspanin macrodomains," Nature Cell Biology, Aug. 1, 2019, pp. 991-1002, vol. 21, No. 8, XP036850071.
Siyuan Wang et al., "Characterization and development of photoactivatable fluorescent proteins for single-molecule-based superresolution imaging," PNAS, Jun. 10, 2014, pp. 8452-8457, vol. 111, No. 23.

*Primary Examiner* — Manjunath N Rao
*Assistant Examiner* — Jae W Lee

(57) ABSTRACT

The present disclosure relates to an exosome comprising a photocleavable protein and a use thereof, and the exosome according to the present disclosure contains a fusion protein comprising a blue fluorescent protein (TagBFP), a photocleavable protein (mMaple3), and an exosome-specific marker protein (CD9), and it has been found that when light of 405 nm is irradiated to the exosome, the photocleavable protein, mMaple3 is cleaved and thereby the blue fluorescent protein in the exosome can be delivered into a target cell. In addition, it has been found that Cre protein in the exosome can be delivered into an animal organ, when light of 405 nm is irradiated to an exosome containing Cre fusion protein (Cre-mMaple3-CD9). Therefore, the exosome containing the photocleavable protein according to the present disclosure is expected to be useful in the protein treatment field by safely and efficiently delivering various therapeutic proteins into cells.

10 Claims, 11 Drawing Sheets

Specification includes a Sequence Listing.

FIG. 6c
| Exosome | Concentration (# particles/mL) | Protein (μg/mL) | Proteins/Particle (ng/particle) |
|---|---|---|---|
| Negative Exosome | $1 \times 10^{11}$ | 1219 | 12.19 |
| TagBFP-mMaple3-CD9 | $3.8 \times 10^{10}$ | 1487 | 39.13 |
FIG. 6d
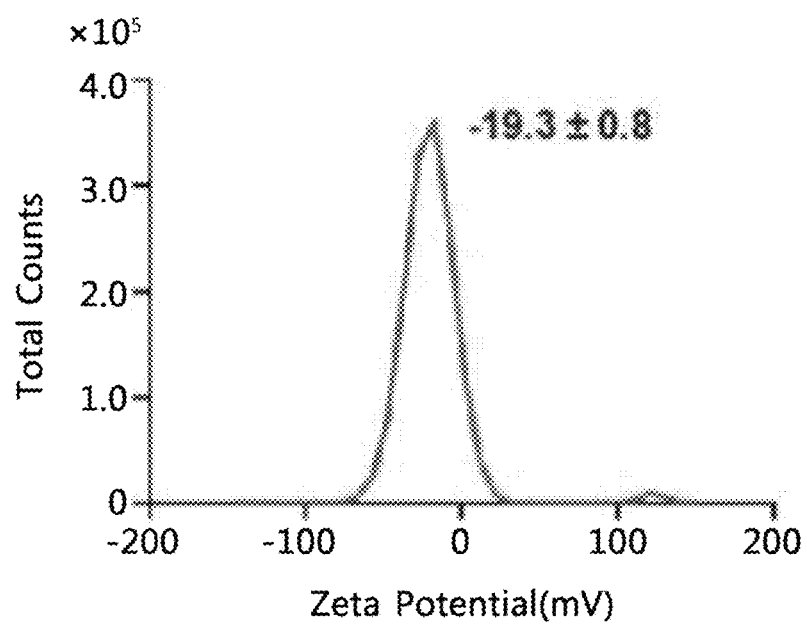
FIG. 6e
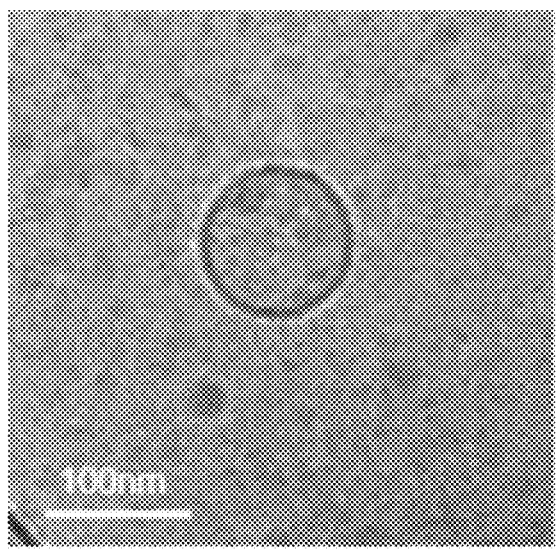

EXOSOME COMPRISING PHOTOCLEAVABLE PROTEIN, AND USE THEREOF

CROSS REFERENCE TO RELATED APPLICATIONS

The present application is a National Phase of International Application No. PCT/KR2021/001634 filed on Feb. 8, 2021, which claims the priority benefit of Korean Patent Application Nos. 10-2020-0015696, filed on Feb. 10, 2020, and 10-2021-0015837, filed on Feb. 4, 2021, in the Korean Intellectual Property Office, the disclosures of which are incorporated herein by reference.

TECHNICAL FIELD

The present disclosure relates to an exosome comprising a photocleavable protein and a use thereof, and more specifically, relates to an exosome containing a fusion protein comprising a target protein and a photocleavable protein, mMaple3 and a use thereof.

The present application claims the priority based on Korean Patent Application No. 10-2020-0015696 filed on Feb. 10, 2020 and Korean Patent Application No. 10-2021-0015837 filed on Feb. 4, 2021, and the entire contents disclosed in the description and drawings of the corresponding applications are incorporated in the present application.

BACKGROUND ART

Most current protein therapies target cell membrane proteins. However, pathogenic factors of many diseases mainly exist inside the cell, and in order to target these pathogenic factors, a technology for delivering a therapeutic protein into the cell is required.

Accordingly, recently, a number of methods for introducing a target protein directly into a cell have been studied, and one of these, a technology of delivery of a therapeutic protein using a lipid nanoparticle has a problem in that the lipid nanoparticle is not effectively separated from the therapeutic protein, and a technology for delivery using a protein transduction domain (PTD) which plays a major role in the intracellular penetration process of viruses has a problem in that the protein transduction domain is degraded when exposed to body fluids such as blood or intestinal fluid.

Therefore, there is a need for a technology for effectively delivering a therapeutic protein to the inside of a cell in order to target pathogenic factors of a specific disease present inside the cell.

On the other hand, an exosome is a vesicle composed of a lipid-bilayer, and is a constituent of a substance secreted by a cell to the outside of the cell. In order to perform a functional role in mediating cell-cell communication and cellular immunity, the exosome is known to play a role of transporting (delivering) a protein, a bioactive lipid and RNA (miRNA) which are biomolecules in a cell. This exosome is also being studied as a biomarker for neurological disease such as Alzheimer, and the like, and is also used in development of a drug delivery system such as a nano-carrier of a specific drug due to high selective permeability enough to penetrate a blood-brain barrier (BBB) that separates cerebrospinal fluid and blood.

With respect to the technology for delivering a therapeutic protein, Korean Patent Publication No. 10-2018-0036134 discloses a method for preparation of an exosome comprising a super-repressor-$I_\kappa$ protein using a light-specific binding protein, and a pharmaceutical composition for preventing and treating inflammatory disease containing the exosome prepared by the method for preparation as an active ingredient, and Japanese Patent Application Publication No. 2019-528674 discloses a method for mass production of an exosome comprising a cargo protein, a vector for preparing the exosome, an exosome comprising a cargo protein prepared by the method, and a method for loading a cargo protein on cytosol by using the exosome prepared thereby.

However, the above documents disclose a light-specific binding protein as a component of a fusion protein in an exosome, and this uses two light-specific binding proteins as CIBN-CRY2 system, so two constructs must be co-transfected when it is expressed in a cell, and therefore the efficiency is lowered, and 488 nm light must be continuously applied to the cell while exosomes are generated, so it may affect the cell, and loss of the amount of a transport protein contained in exosomes occurs. In addition, there are disadvantages in that when binding of CIBN and CRY2 is maintained in absence of light after exosome formation, the transport protein cannot move freely and may be bound to an exosome-specific protein, and the size of CRY2 to be fused to the transport protein is big as 65 kDa, so it may affect the intrinsic function of the transport protein, and in order to confirm whether it is expressed well in a cell, a fluorescent protein such as EGFP must be fused separately and used, and there is no way to confirm whether the binding of CRY2 and CIBN is fallen when no light is given.

Accordingly, the present inventors have attempted to overcome disadvantages of the conventionally known protein delivery technology using the CIBN-CRY2 system and develop a method for safely and effectively delivering a protein into a cell.

DISCLOSURE

Technical Problem

The Sequence Listing created on Jul. 25, 2022 with a file size of 11.00 KB, and filed herewith in ASCII text file format as the file entitled "SequenceListing_421PO0017US.TXT," is hereby incorporated by reference in its entirety.

The present inventors have found that when light is irradiated to an exosome containing a fusion protein where photocleavable protein mMaple3 is combined with a target protein to be delivered into a cell, the mMaple3 is cleaved to safely and efficiently release the target protein in the exosome into a target cell, thereby completing the present disclosure based on this.

Accordingly, an object of the present disclosure is to provide an exosome containing a fusion protein comprising a target protein, a photocleavable protein and an exosome-specific marker protein and a use thereof.

However, a technical problem to be achieved by the present disclosure is not limited to the aforementioned problems, and other problems not mentioned can be clearly understood by those skilled in the art to which the present disclosure pertains from the description below.

Technical Solution

In order to achieve the above objects, the present disclosure provides an exosome containing a fusion protein comprising a target protein and mMaple3.

In addition, the present disclosure provides a composition for delivery of a target protein into a cell, comprising the exosome as an active ingredient.

Moreover, the present disclosure provides a method for delivering a target protein into a cell in vitro, comprising irradiating light to an exosome containing a fusion protein comprising a target protein and mMaple3; and treating the light-irradiated exosome to a target cell.

Furthermore, the present disclosure provides a screening method of a protein candidate drug for delivery into a cell, comprising (a) irradiating light to an exosome containing a fusion protein comprising a protein candidate drug and mMaple3:

(b) treating the light-irradiated exosome to a target cell; and (c) confirming that the protein candidate drug is delivered into the cell, when the mMaple3 exhibits fluorescence in the target cell.

As one embodiment of the present disclosure, the fusion protein may further comprise an exosome-specific marker protein.

In addition, the present disclosure provides a method for preparation of the fusion protein, comprising the following steps:

(S1) amplifying cDNA of a target protein and mMaple3, respectively:

(S2) combining the amplified cDNA of the target protein and mMaple3 into one cDNA, to prepare cDNA encoding a fusion protein comprising the target protein and mMaple3; and (S3) expressing the fusion protein by introducing cDNA encoding the fusion protein into a vector and then transfecting it into a cell.

Furthermore, the present disclosure provides a method for preparation of the exosome, comprising the following steps:

(S1) amplifying cDNA of a target protein and mMaple3, respectively:

(S2) combining the amplified cDNA of the target protein and mMaple3 into one cDNA, to prepare cDNA encoding a fusion protein comprising the target protein and mMaple3; and (S3) transfecting cDNA encoding the fusion protein into an exosome-producing cell, and separating and purifying an exosome from a cell culture medium.

As one embodiment of the present disclosure, it may comprise combining the amplified cDNA of mMaple3 and cDNA of an exosome-specific marker protein into one cDNA, before combining the amplified cDNA of the target protein and mMaple3 into one cDNA in the (S2).

As another embodiment of the present disclosure, the separation of the exosome in the (S3) may use one method selected from the group consisting of TFF (tangential flow filtration), ultracentrifugation, size exclusion chromatography, and exosome isolation kit.

As other embodiment of the present disclosure, the mMaple3 may comprise the amino acid sequence of SEQ ID NO: 1.

As other embodiment of the present disclosure, the mMaple3 may be encoded by a gene comprising the nucleotide sequence of SEQ ID NO: 2.

As other embodiment of the present disclosure, the target protein may be a protein to be delivered into a cell.

As other embodiment of the present disclosure, the target protein may be a protein for treating disease or a protein for diagnosing disease.

As other embodiment of the present disclosure, the exosome-specific marker protein may be one or more selected from the group consisting of CD9, CD63, and CD81.

As other embodiment of the present disclosure, the mMaple3 in the exosome may be cleaved through the step of irradiating light to the exosome.

As other embodiment of the present disclosure, the light may have a wavelength of 401 nm to 480 nm.

In addition, the present disclosure provides a method for delivery into a cell of a target protein, comprising a method for administering a composition comprising an exosome containing a fusion protein comprising a target protein and mMaple3 into a subject.

Moreover, the present disclosure provides a use for delivering a target protein into a cell, of a composition comprising an exosome containing a fusion protein comprising a target protein and mMaple3.

Furthermore, the present disclosure provides a use of an exosome containing a fusion protein comprising a target protein and mMaple3, for production of a preparation for delivery into a cell of a target protein.

Effects

The exosome according to the present disclosure contains a fusion protein comprising a blue fluorescent protein (TagBFP), a photocleavable protein (mMaple3), and an exosome-specific marker protein (CD9), and it has been confirmed that when light of 405 nm is irradiated to the exosome, the photocleavable protein, mMaple3 is cleaved and thereby the blue fluorescent protein in the exosome can be delivered into a target cell. In addition, it has been confirmed that Cre protein in the exosome can be delivered into an animal organ, when light of 405 nm is irradiated to an exosome containing Cre fusion protein (Cre-mMaple3-CD9). Therefore, the exosome containing the photocleavable protein according to the present disclosure is expected to be usefully used in the protein treatment field by safely and efficiently delivering various therapeutic proteins into cells.

BRIEF DESCRIPTION OF THE DRAWINGS

FIG. 6c is the result of measuring the concentration of the exosome containing the fusion protein (TagBFP-mMaple3-CD9) according to one embodiment of the present disclosure by microBCA.

FIG. 6d is the result of measuring the zeta potential of the exosome containing the fusion protein (TagBFP-mMaple3-CD9) according to one embodiment of the present disclosure.

FIG. 6e is the result of cryogenic electron microscopy (Cryo-TEM) image observation of the exosome containing the fusion protein (TagBFP-mMaple3-CD9) according to one embodiment of the present disclosure.

MODE FOR INVENTION

Figure 1:
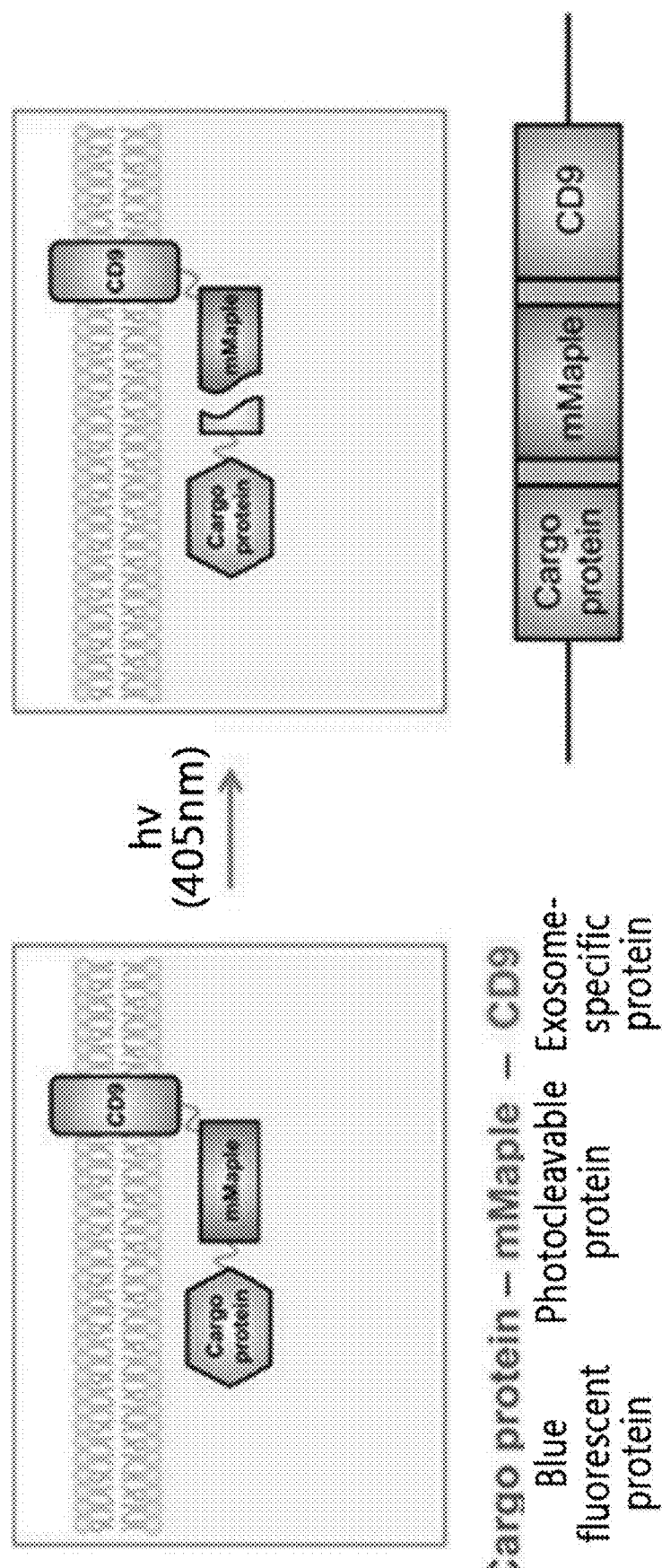
FIG. 1 schematically shows the structure of the fusion protein in which the target protein (blue fluorescent protein), photocleavable protein and exosome-specific marker protein are combined according to one embodiment of the present disclosure and characteristics thereof.

The present disclosure provides an exosome containing a fusion protein comprising a target protein and mMaple3.

In addition, the present disclosure provides a composition for delivery of a target protein into a cell, comprising the exosome as an active ingredient.

Furthermore, the present disclosure provides a method for preparation of the fusion protein comprising the following steps:
(S1) amplifying cDNA of a target protein and mMaple3, respectively:
(S2) combining the amplified cDNA of the target protein and mMaple3 into one cDNA, to prepare cDNA encoding a fusion protein comprising the target protein and mMaple3; and
(S3) expressing the fusion protein by introducing cDNA encoding the fusion protein into a vector and then transfecting it into a cell.

In addition, the present disclosure provides a method for preparation of the exosome comprising the following steps:
(S1) amplifying cDNA of a target protein and mMaple3, respectively:
(S2) combining the amplified cDNA of the target protein and mMaple3 into one cDNA, to prepare cDNA encoding a fusion protein comprising the target protein and mMaple3; and
(S3) transfecting cDNA encoding the fusion protein into an exosome-producing cell, and separating and purifying an exosome from a cell culture medium.

In the present disclosure, it may comprise combining the amplified cDNA of mMaple3 and cDNA of an exosome-specific marker protein into one cDNA, before combining the amplified cDNA of the target protein and mMaple3 into one cDNA in the (S2).

In the present disclosure, the (S3) may be transfecting the cDNA encoding the fusion protein into an exosome-producing cell and replacing a cell culture medium with an FBS-free DMEM medium comprising penicillin/streptomycin and then collecting the medium, and separating and purifying an exosome from the collected medium.

In the present disclosure, the separation of the exosome in the (S3) may use one method selected from the group consisting of TFF (tangential flow filtration), ultracentrifugation, size exclusion chromatography, and exosome isolation kit, but not limited thereto.

In the present disclosure, "fusion protein" is a protein produced by fusion of two or more proteins, and may comprise a target protein and mMaple3, and may further comprise an exosome-specific marker protein. The target protein, mMaple3, and exosome-specific marker protein composing the fusion protein may be in a form combined into one, and for example, it may be in an order of the target protein-mMaple3-exosome-specific marker protein in order, and when tracking of the target protein is needed, it may be in an order of the exosome-specific marker protein-mMaple3-target protein, but there is no limitation on their binding order.

In the present disclosure, "target protein" is a protein present in an exosome in a form combined to a photocleavable protein, and means a protein to be delivered into a target cell or tissue. The target protein may be a protein for treating disease or a protein for diagnosing disease, and there is no limitation on type thereof. For example, a cancer inhibiting protein, p53 is delivered into a cancer cell as a target protein, and thereby, an effect of treating cancer may be exhibited, and an effect for treating Parkinson's disease may be exhibited by delivering a normal parkin protein into a neuron for Parkinson's disease caused by abnormal function due to mutation occurring in the parkin protein, and in the research of next-generation stem cell therapies, Oct4, Sox2, c-Myc, and Klf4 proteins as Yamanica factors which are proteins required in the most important process, a process of dedifferentiating a patient's somatic cell into a stem cell are delivered into the patient's somatic cell, and thereby, dedifferentiation into a stem cell is possible without a virus currently used for stem cell dedifferentiation. In addition, through delivery of a myodifferentiation inducing protein such as Myogenin and MyoD as a target protein, a therapeutic effect for degenerative muscle disease such as muscular dystrophy characterized by progressive muscle weakness, atrophy and muscle fiber necrosis, and the like may be shown, and through delivery of NRF2 and BDNF proteins known as having a protective effect of a cranial nerve in dementia, one of neurodegenerative diseases, a therapeutic effect for dementia may be exhibited, and through delivery of a brown fat inducing factor such as PGC1α, PPAR-γ which differentiate a white fat cell into a brown fat cell, a therapeutic effect for metabolic disease may be shown. In one embodiment of the present disclosure, using a blue fluorescent protein, TagBFP, delivery thereof into a cell has been confirmed, and using Cre protein, delivery thereof into an animal organ has been confirmed.

In the present disclosure, "delivery into a cell of a target protein" means transferring a target protein present in a form combined to a photocleavable protein in an exosome into the inside of a targeted cell from the exosome.

In the present disclosure, "mMaple3" is a photocleavable protein, and the "photocleavable protein" means a protein which is cleaved when exposed to light with a specific wavelength.

In the present disclosure, the mMaple3 may comprise the amino acid sequence of SEQ ID NO: 1, and may be encoded by a gene comprising the nucleotide sequence of SEQ ID NO: 2.

In the present disclosure, "exosome-specific marker protein" is a protein positioned at the exosome outer membrane, and for example, it may be one or more selected from the group consisting of CD9, CD63, and CD81, and according to one embodiment of the present disclosure may be CD9, but not limited thereto.

In the present disclosure, the CD9 may comprise the amino acid sequence of SEQ ID NO: 3, and may be encoded by a gene comprising the nucleotide sequence of SEQ ID NO: 4.

In the present disclosure, "exosome" is a membrane vesicle having a membrane structure composed of lipid bilayers secreted to the outside of a cell as collecting protein, DNA, RNA, and the like, for signaling between cells, and is present in body fluids in almost all eukaryotes. The diameter of the exosome may be 10 nm to 400 nm, 10 nm to 350 nm, 10 nm to 300 nm, 10 nm to 250 nm, 10 nm to 200 nm, 10 nm to 150 nm, 50 nm to 350 nm, 50 nm to 300 nm, 50 nm to 250 nm, 50 nm to 200 nm, 50 nm to 150 nm, 100 nm to 300 nm, 100 nm to 200 nm, or 100 nm to 150 nm, and when a multiple vesicle is fused with a cell membrane, it is released from a cell, or it is released from a cell membrane immediately.

The exosome may be prepared by using a method for extracting an exosome known in the art, and there is no limitation on the method for extracting.

In addition, the present disclosure provides a method for delivery into a cell of a target protein in vitro, comprising irradiating light to an exosome containing a fusion protein comprising a target protein and mMaple3; and
treating the light-irradiated exosome to a target cell.

In addition, the present disclosure provides a screening method of a protein drug for delivery into a cell, comprising (a) irradiating light to an exosome containing a fusion protein comprising a protein candidate drug and mMaple3:
(b) treating the light-irradiated exosome to a target cell; and
(c) identifying the protein candidate drug as protein drug delivered into the cell, if the mMaple3 exhibits fluorescence in the target cell.

In the present disclosure, the mMaple3 in the exosome may be cleaved through the irradiating light into the exosome, and then, the light may have a wavelength of 401 nm to 480 nm, 401 nm to 470 nm, 401 nm to 460 nm, 401 nm to 450 nm, 401 nm to 440 nm, 401 nm to 430 nm, 401 nm to 420 nm, or 401 nm to 410 nm, and light of 400 nm or less is ultraviolet light (UV) and may damage it when treated to a cell or exosome, and light with a wavelength over 480 nm may also affect it when treated to a cell. In the present disclosure, there is no limitation on the wavelength of light as long as it is within a range of 401 nm to 480 nm, but according to one embodiment of the present disclosure, preferably, it may be 405 nm.

In the present disclosure, in the (c), the mMaple3 may exhibit green fluorescence when it is not cleaved, and may exhibit red fluorescence when cleaved.

In addition, the present disclosure provides a method for delivery into a cell of a target protein, comprising administering a composition comprising an exosome containing a fusion protein comprising a target protein and mMaple3 into a subject.

In the present disclosure, "subject" means a subject in need of the target protein, and more specifically, it means a primate which is a human or non-human, or a mammal such as a mouse, a dog, a cat, a horse and a cow.

In the present disclosure, "administration" means providing the prescribed composition of the present disclosure into a subject by any appropriate method.

Furthermore, the present disclosure provides a use for delivering a target protein into a cell, of the composition comprising an exosome containing a fusion protein comprising a target protein and mMaple3.

In addition, the present disclosure provides a use of the exosome containing a fusion protein comprising a target protein and mMaple3, for producing a preparation for delivering a target protein into a cell.

In one example of the present disclosure, a fusion protein (TagBFP-mMaple3-CD9) in which a blue fluorescent protein (TagBFP), a photocleavable protein (mMaple3) and an exosome-specific marker protein (CD9) were combined was prepared, and an advantage shown when the mMaple3 was used compared to other photocleavable protein types, and an advantage shown by the mMaple system compared to the CIBN-CRY2 system were confirmed (See Example 1).

In another example of the present disclosure, it was confirmed that the mMaple3 was cleaved by light of 405 nm, when the fusion protein (TagBFP-mMaple3-CD9) was overexpressed in the HEK293T cell, and then light of 405 nm was irradiated (See Example 2).

In other example of the present disclosure, it was confirmed that the mMaple3 was cleaved by light of 405 nm, when the exosome was separated and purified from the medium of the HEK293T cell in which the fusion protein (TagBFP-mMaple3-CD9) was overexpressed (See Example 3).

In other example of the present disclosure, as the result of confirming degradation of a target protein according to presence or absence of treatment of Triton X-100, proteinase (proteinase K) and light of 405 nm to an exosome containing the fusion protein (TagBFP-mMaple3-CD9), it was confirmed that the target protein was not degraded by proteinase and light of 405 nm did not affect the lipid bilayers of the exosome, unless artificially permeable to the lipid bilayers of the exosome by treating Triton X-100 (See Example 4).

In one experimental example of the present disclosure, it was confirmed that the blue fluorescent protein was delivered into a cell, when light of 405 nm was irradiated to the exosome containing the fusion protein (TagBFP-mMaple3-CD9) and this was treated to the HEK293T cell (See Experimental example 1).

In one experimental example of the present disclosure, it was confirmed that the Cre protein in the exosome was delivered into an organ of a mouse, when light of 405 nm was irradiated to the exosome containing the Cre fusion protein (Cre-mMaple3-CD9) and this was administered into a genetically modified mouse in which the red fluorescent protein (tdTomato) was expressed when the Cre protein was delivered (See Experimental example 2).

Hereinafter, in order to help understanding of the present disclosure, preferable examples and experimental examples are suggested. However, the following examples and experimental examples are provided only to understand the present disclosure more easily, but the content of the present disclosure is not limited by the following examples and experimental examples.

Example 1. Fusion Protein Preparation and Photocleavable Protein Characteristic Comparison 1-1. Fusion Protein Preparation cDNA encoding the fusion protein (TagBFP-mMaple3-CD9) in which the blue fluorescent protein (TagBFP), photocleavable protein (mMaple3) and exosome-specific marker protein (CD9) were combined was prepared, and the structure of the fusion protein translated from the prepared cDNA and characteristics thereof were schematically shown in FIG. 1, and the amino acid sequences of each of the TagBFP, mMaple3, and CD9 and the gene sequences encoding them were shown in Table 1 below.

TABLE 1

| | sequences | SEQ ID Number |
|---|---|---|
| mMaple3 amino acid sequence | MVSKGEETIMSVIKPDMKIKLRMEGNVNQHAFVIEGEGSQK PFBGIQTIDLEVKEGAPLPPAYDILTTAPHYGNRVFTKYPRKI PDYFKQSFPEGYSWERSMTYEDGGICNATNDITMEEDSFINK IHFKGTNFPPNGPVMQKRTVGWEVSTEKMYVRDGVLKGDV KMKLLLKGQSHYRCDFRTTYKVKQKAVKLPKAHFVDHRIEI LSHDKDYNKVKLYEHAVARNSTDSMDELYK | 1 |
| mMaple3 DNA sequence | ATGGTGAGCAAAGGCGAGGAGACAATCATGTCCGTGATC AAGCCCGACATGAAGATCAAACTGAGGATGGAGGGCAAC GTGAACGGCCACGCCTTGGTGATCGAGGGCGAAGGAAGC GGCAACCCCTTCGAGGGCATCCAGACCATCGATCTGGAG CTCAAGGAGGGCGCTCCCCTCCCTTTCGCCTATGACATCC TGACCACCGCCTTCCACTACGGCAATAGGGTGTTCACCAA GTATGCCAGGAAGATCCCCGACTACTTCAAGCAGAGCTTC CCTGACCGCTACAGCTGGGAGAGGAGCATGACATACGAG GACGGCGGCATCTGCAACGCCACCAACGACATCACAATG GAGGAGGACAGCTTCATCAACAAGATCCACTTCAAAGGG ACAAACTTCCGCCGGAATGGCCCCGTGATGCAGAAGAGG ACCGTGGGCTGGGAGGTGAGCACCGAGAAGATGTACGTG AGGGACGGCGTCCTGAAGGGCGACGTGAAGATGAAGCTC CTGCTCAAGGGGGGCAGCCACTACAGGTGCGACTTTAGG ACCACCTATAAGGTGAAGCAGAAGGCTGTGAAGCTGGCC AAGGCCCACTTCGTCGACCATAGGATCGAGATCCTGTCCC ACGACAAGGACTACAACAAGGTCAAGCTGTACGAGCACG CCGTCCCTAGGAACAGCACCGACAGCATGGACGAACTCT ATAAG | 2 |
| CD9 amino acid sequence | MPVKGGTKCIKYLLFGFNFIFWLAGIAVLAIGLWLRFDSQTK SIFEQETNNNNSSFYTGVYILIGAGALMMLVGFLGCCGAVQE SQCMLGIFFGFLLVIFAIEIAAAIWGYSHKDEVIKEVQEFYKD TYNKLKTKDEPQRETLKAIHYALNCQGLAGGVEQFISDICPK KDVLETFTVKSCPDAIKEVEDNKFHIIGAVGIGIAVVMIFGMI FSMILCCAIRRNREMV | 3 |
| CD9 DNA sequence | ATGCCGGTCAAAGGAGGCACCAAGTGCATCAAATACCTG CTGTTCGGATTTAACTTCATCTTCTGGCTTGCCGGGATTGC TGTCCTTGCCATTGGACTATGGCTCCGATTCGACTCTCAG ACCAAGAGCATCTTGGAGCAAGAAACTAATAATAATAAT TCCAGCTTCTACACAGGAGTCTATATTCTGATCGGAGCGG CCCCCCTCATGATGCTGGTGGGCTTCCTGGGCTGCTGCGG GGCTGTGCAGGAGTCCCAGTGCATGCTGGGACTGTTCTTC GGCTTGCTCTTGGTGATATTCGCCATTGAAATAGCTGCGG CCATCTGGGGATATTCCCACAAGGATGAGGTGATTAAGG AAGTCCAGGAGTTTTACAAGGACACCTACAACAAGCTGA AAACCAAGGATGAGCCCCAGCGGGAAACGCTGAAAGCCA TCCACTATGCGTTGAACTGCTGTGGTTTGGCTGGGGCGT GGAACAGTTTATCTCAGACATCTGCCCCAAGAAGGACGTA CTCGAAACCTTCACCGTGAAGTCCTGTCCTGATGCCATCA AAGAGGTCTTCGACAATAAATTCCACATCATCGGCGCAGT GGGCATCGGCATTGCCGTGGTCATGATATTTGGCATGATC TTCACTATGATCTTGTGCTGTGCTATCCGCAGGAACCGGG AGATGGTC | 4 |
| TagBFP amino acid sequence | MSELIKENMHMKLYMEGTVDNHHFKCTSEGEGQKPYEGTQT MRIKVVEGGPLPFAFDILATSFLYGSKTFINHTQGIPDFFKQSF PEGFTWERVTTYEDGGVLTATQDISLQDGCLTYNYKIRQVN FISNGPVMQKKTLGWEAFTETLYPADGGLEGRNDMALKLV GGSHLIANIKTTYRSKKPAKNLKMPQVYYVDYRLERIKEAN NETYVEQHEVAVARYCDLPSKLGHKLN | 5 |

TABLE 1-continued

| sequences | | SEQ ID Number |
|---|---|---|
| TagBFP DNA sequence | ATGAGCGAGCTGATTAAGGAGAACATGCACATGAAGCTG TACATGGAGGGCACCGTGGACAACCATCACTTCAAGTGC ACATCCGAGGGCGAAGGCAAGCCCTACGAGGGCACCCAG ACCATGAGAATCAAGGTGGTCGAGGGGGGCCCTCTCCCCT TCGCCTTCGACATCCTGGCTACTAGCTTCCTCTACGGCAG CAAGACCTTCATCAACCACACCCAGGGCATCCCCGACTTC TTCAAGCAGTCCTTCCCTGAGGGCTTCACATGGGAGAGAG TCACCACATACGAAGACGGGGGCGTGCTGACCGCTACCC AGGACACCAGCCTCCAGGACGGCTGCCTCATCTACAACGT CAAGATCAGAGGGGTGAACTTCACATCCAACGGCCCTGT GATGCAGAAGAAACACTGGGCTGGGAGGGCTTCACCGA GACGCTGTACCCCGCTGACGGCGGCCTGGAAGGCAGAAA CGACATGGCGCTGAAGCTCGTGGGCGGGAGCCATCTGATC GCAAACATCAAGACCACATATAGATCCAAGAAACCCGCT AAGAACCTCAAGATGCCTGGCGTCTACTATGTGGACTACA GACTGGAAAGAATCAAGGAGGCCAACAACGAGACCTACG TCGAGCAGCACGAGGTGGCAGTGGCCAGATACTGCGACC TGCCTAGCAAACTGGGGCACAAGCTTAAT | 6 |

Specifically, at first, cDNA encoding TagBFP, mMaple3 and CD9 was prepared and amplified by PCR, respectively, and cDNA of the amplified mMaple3 and CD9 was combined into one cDNA (mMaple3-CD9) by PCR. Then, mMaple3-CD9 cDNA and TagBFP cDNA were combined into one cDNA (TagBFP-mMaple3-CD9) by PCR to produce cDNA encoding a fusion protein. The primers used in the present disclosure were shown in Table 2 below.

TABLE 2

| DNA fragment for cloning | Primer sequence | SEQ ID Number |
|---|---|---|
| TagBEP-Linker | F: TATGCTGAATTCGCCACCATGAGCGAG R: GGAAGCTTGAGCTCGAGATCTGAGTCCGGAATTAA GCTTGTGCCCCAGTTTG | 7 |
| Linker-mMaple3-Linker | F: TCTCGAGCTCAAGCTTCCGTGAGCAAAGGCGAGGA G | 9 |
| | R: ACCTCCGCCTGAACCGCCACCTCCCGACTTATAGA GTTCGTCCATGCTGTC | 10 |
| Linker-CD9 | F: GGCGGTTCAGGCGGAGGTGGCTCTGGCGGTGGCG GATCGCCGGTCAAAGGAGGCAC | 11 |
| | R: CCCTCTAGTCTAGAGACCATCTCGCGGTTCC | 12 |

Figure 2:
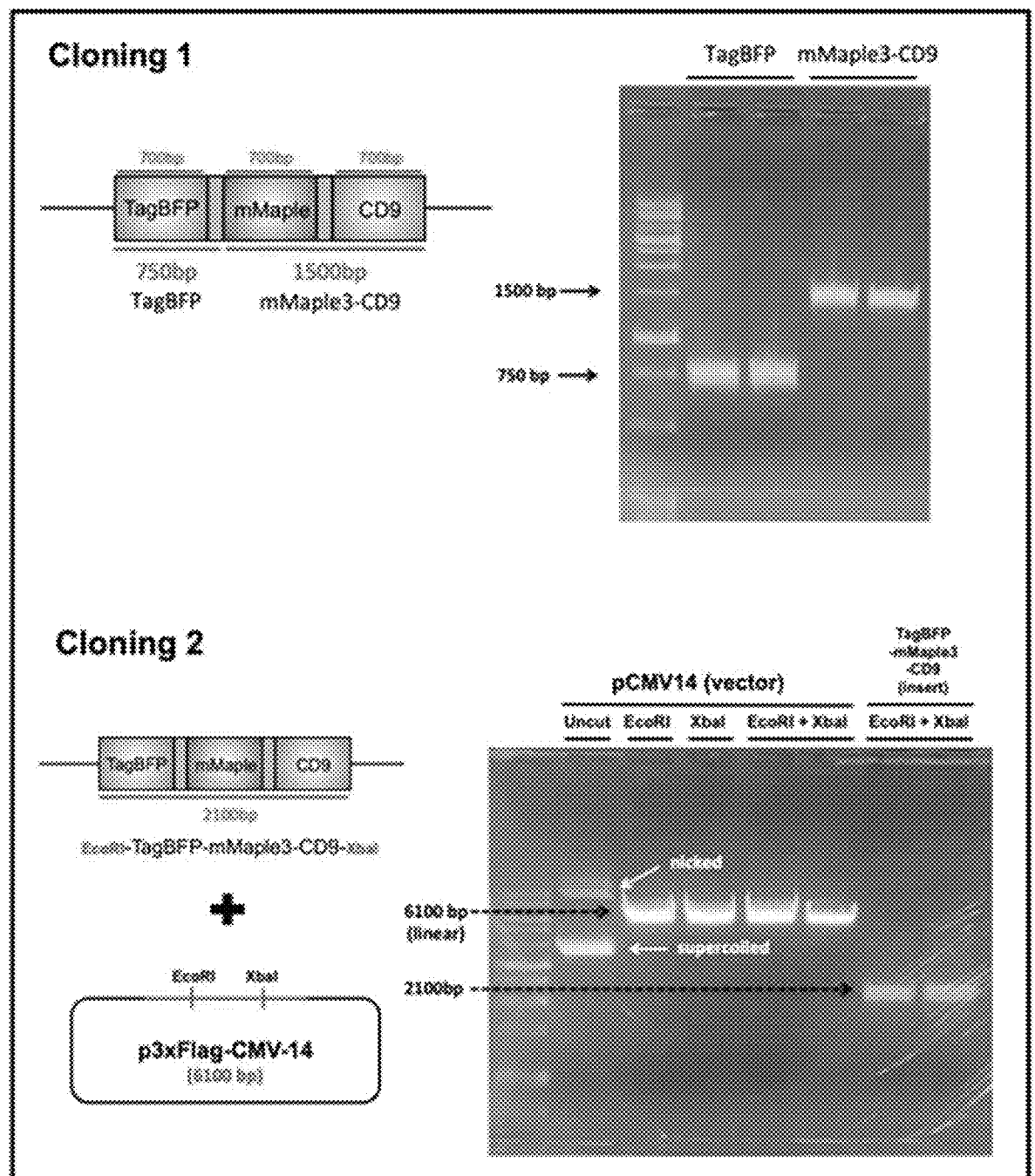
FIG. 2 shows the process of preparation and the result of confirming expression in a cell of the fusion protein (TagBFP-mMaple3-CD9) according to one embodiment of the present disclosure.

After that, cDNA encoding a fusion protein was cloned by using EcoR1 and Xba1 restriction enzymes into pCMV14 vector so that the fusion protein was expressed in Mammalia cell. When the pCMV14-TagBFP-mMaple3-CD9 was transfected into the HEK293T cell by using PEI (polyethylenimine), as shown in FIG. 2, expression of the fusion protein was confirmed.

1-2. Comparison of Characteristics According to Photocleavable Protein Types

By comparing characteristics of various kinds of photocleavable proteins (PAFP) such as Dendra2, mEos2, tdEos, mKikGR, and Kaede, and the like, and mMaple3 by referring to conventional documents (S. Wang, et al, Proc. Natl. Acad. Sci. U.S.A. 111, 8452-8457 (2014)), an advantage shown by the mMaple3 when compared to other photocleavable proteins was confirmed.

As a result, as shown in Table 3 below, it was confirmed that many photocleavable proteins generally had strong tendency to form oligomers in oligomerization tendency and cohesion, whereas mMaple3 had strong tendency to maintain monomers and weak cohesion.

Regarding the result of Switch λ showing a wavelength of light for cleavage, it was confirmed that KikGR and Kaede required light of 400 nm or less to be cleaved, and 400 nm or less is UV (ultraviolet light) and may damage it when treated to a cell or exosome, whereas in case of irradiating light of 400 nm or more, it was safer when it was cleaved after expressing in a cell or it was cleaved by adding to the exosome, and the mMaple3 was cleaved with light of 400 nm or more.

Among the photocleavable proteins expressed in a cell, there may be photocleavable proteins that are not fully folded until fluorescence is measured, and among the photocleavable proteins that have been fully folded, only some of them are cleaved by light to show fluorescence, and it could be confirmed that the efficiency of being cleaved and showing fluorescence was superior to that of other photocleavable protein as the mMaple3 had a high level of No. of localizations per cell showing the number of PAFP (photoactivatable fluorescent protein) detected by fluorescence per cell/the expression level of actual PAFP.

In addition, while most photocleavable proteins have acid sensitivity, there was no reported acid sensitivity in case of mMaple3.

TABLE 3

| PAFP | Oligomerization | Clustering | Switch λ (nm) | No. of localizations per cell | Add Sensitivity |
|---|---|---|---|---|---|
| Dendra2 | Monomer | − | 405,480 | 1,810 | High |
| mEos2 | Weak dimer | + | 405 | 1,290 | Moderate |
| tdEos | Tetramer | − | 405 | 1,800 | NA |
| mKikGR | Monomer | + | 390 | 3,800 | High |
| Kaede | Tetramer | + | 380 | NA | Moderate |
| mMaple3 | Monomer | − | 405 | 12,300 | NA |

1-3. Comparison of CIBN-CRY2 System and mMaple System

Figure 3A:
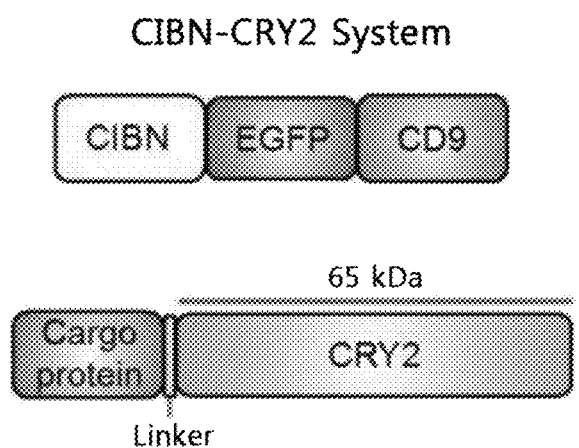
FIG. 3a briefly schematically shows the CIBN-CRY2 system.
Figure 3B:
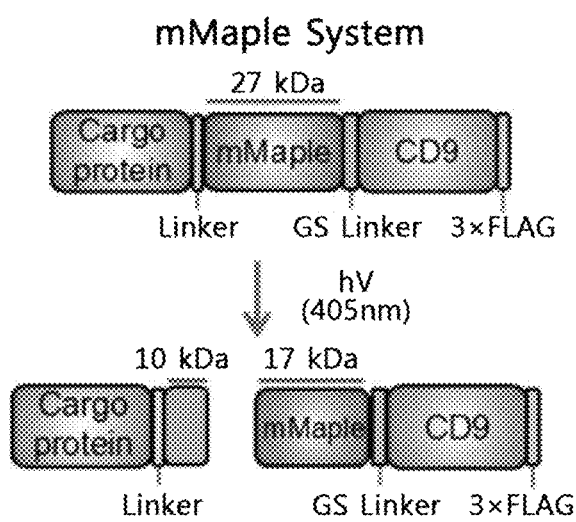
FIG. 3b briefly schematically shows the mMaple system according to one embodiment of the present disclosure.

The CIBN-CRY2 system shown in FIG. 3a uses two light-specific binding proteins, so two constructs should be always used, and in this case, as two constructs should be co-transfected, the efficiency is lowered. For example, when the transfection efficiency is 80%, the probability that all the two constructs are transfected into one cell becomes 64%. On the other hand, the mMaple system shown in FIG. 3b uses one construct, so it is possible to express it in a cell with better efficiency.

In addition, the CIBN-CRY2 system has disadvantages in that it may affect a cell as light of 488 nm should be continuously applied into the cell during producing an exosome, and loss of the amount of the transport protein contained in the exosome is caused as the binding efficiency of CIBN and CRY2 by light cannot be 100%, but the mMaple system is safe as the transport protein is fused to a photocleavable protein and an exosome-specific marker at the beginning and therefore there is no transport protein loss when a cell forms an exosome, and light is not required to be applied directly to the cell.

Furthermore, in the CIBN-CRY2 system, the case in that the binding of CIBN and CRY2 is not maintained under the condition without light after forming an exosome may occur and in this case, the transport protein cannot move freely and may be bound to the exosome-specific protein, whereas the mMaple system cleaves the photocleavable protein by applying light to the exosome after forming an exosome, and then, the efficiency to be cleaved is very high, and when the cleavage efficiency is high, it means that a lot of transport proteins the can move freely are generated in the exosome.

Moreover, the CIBN-CRY2 system has disadvantages in that it cannot affect the intrinsic function of the transport protein as the size of CRY2 is big as 65 kDa, and a fluorescent protein such as EGFP should be fused and used separately to confirm whether it is expressed well in a cell, and there is no way to confirm whether the binding of CRY2 and CIBN is broken when light is not given, while the mMaple system has very low possibility to affect the intrinsic function of the transport protein as the size of the photocleavable protein fragment attached to the transported protein after being cleaved is just 10 kDa, and whether it is expressed properly in a cell can be confirmed by green fluorescence as the photocleavable protein itself is a fluorescent protein, and whether the photocleavable protein is delivered well can be confirmed by red fluorescence after treating light to the exosome.

As above, when the photocleavable protein mMaple3 according to the present disclosure is comprised in the fusion protein, compared to the case in that other type of photocleavable protein and a light-specific binding protein of the CIBN-CRY2 system are comprised, the advantage as in Examples 1-2 and 1-3 above are shown, and accordingly, an effect of protein delivery into a cell was confirmed by an experiment using a fusion protein comprising the photocleavable protein mMaple3 of the present disclosure.

Example 2. Confirmation of Delivery of Fusion Protein 24 hours after seeding the HEK293T cell, the TagBFP-mMaple3-CD9 cDNA was transfected using PEI by the method of Example 1-1 above to overexpress it into the HEK293T cell, and then an effect of cleavage by light was confirmed by a confocal microscope and western blot in the HEK293T cell by irradiating light of 405 nm.

Figure 4A:
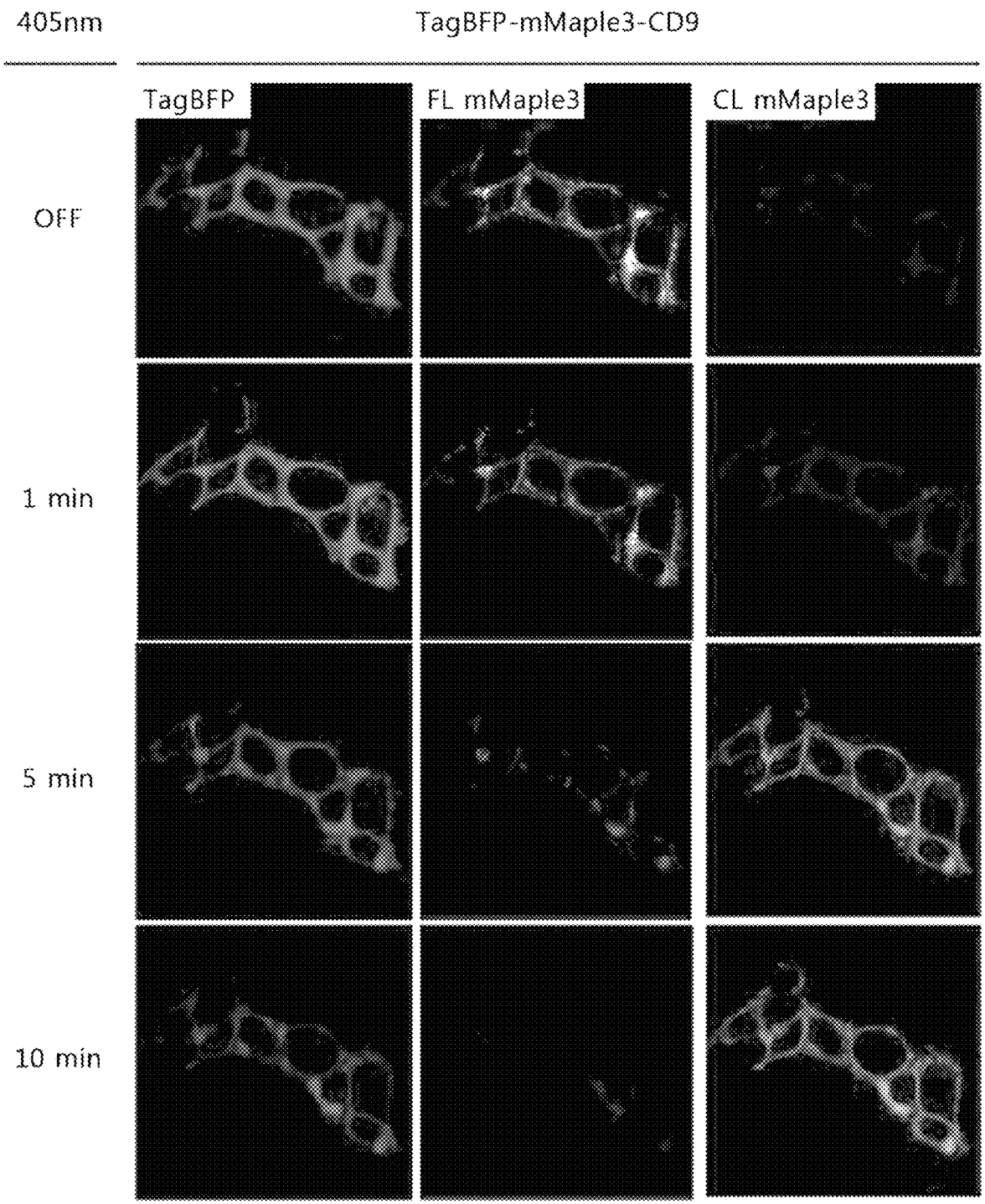
FIG. 4a is the result of confirming the cleavage effect by light irradiation of the fusion protein (TagBFP-mMaple3-CD9) in the HEK293T cell according to one embodiment of the present disclosure through a confocal microscope.
Figure 4B:
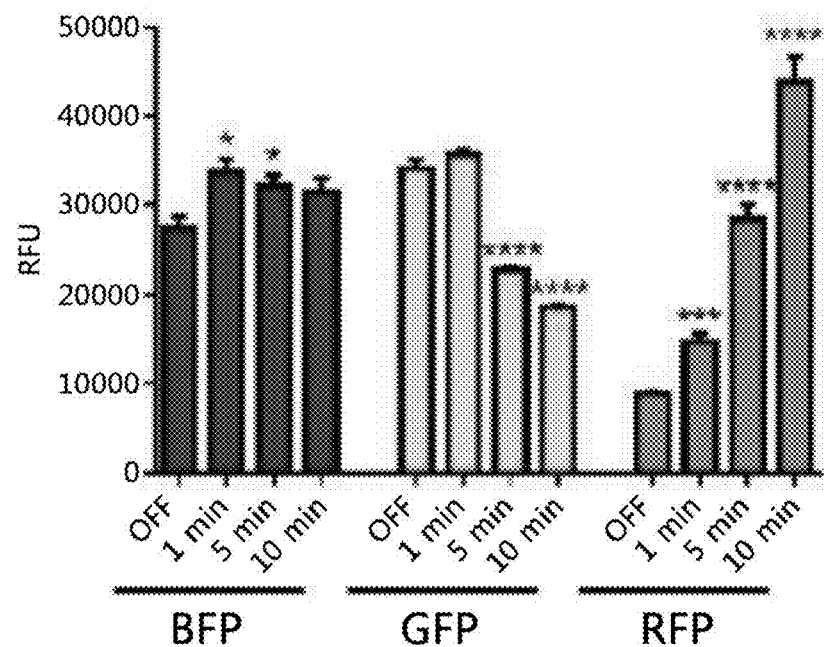
FIG. 4b shows the intensity of fluorescence shown in FIG. 4a above as a graph.

The experimental result of confocal microscope observation confirmed the expression of the fusion protein using a confocal microscope (LSM700), 24 hours after transfection by blue fluorescence (TagBFP) and green fluorescence (mMaple3) in FIG. 4a, and confirmed the delivery of the fusion protein by the reduced intensity of green fluorescence (mMaple3 before cleaved) and the increased intensity of red fluorescence (mMaple3 after cleaved), and the intensity of the fluorescence was measured and shown in FIG. 4b.

As a result, as shown in FIGS. 4a and 4b, considering that green fluorescence of the mMaple3 itself was shown before irradiating light of 405 nm and red fluorescence was shown after irradiating light of 405 nm, it could be confirmed that the mMaple3 protein was cleaved, and it was confirmed that the longer the 405 nm light was irradiated, the more the photocleavable protein (mMaple3) was cleaved, so the green fluorescence was decreased and red fluorescence was increased.

Figure 4C:
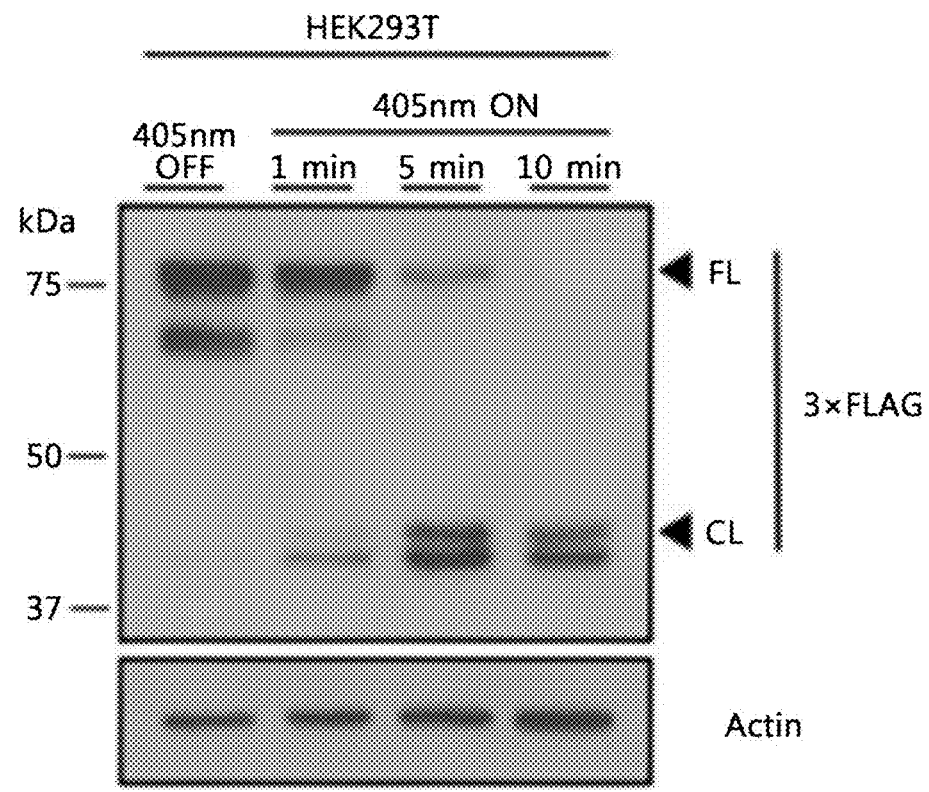
FIG. 4c is the result of confirming the cleavage effect by light irradiation of the fusion protein (TagBFP-mMaple3-CD9) in the HEK293T cell according to one embodiment of the present disclosure by western blot.

In addition, light of 405 nm was irradiated into a cell for 5 minutes, 24 hours after transfection using western blot and the protein was extracted using T-per buffer, and the extracted protein was separated by electrophoresis and then the expression of the fusion protein and cleavage of the fusion protein by light of 405 nm were confirmed, and as a result, as shown in FIG. 4c, by observing that after irradiating light of 405 nm, the amount of the fusion protein not cleaved was reduced over time, whereas the amount of the cleaved fusion protein section was increased, the effect of cleavage of the mMaple3 protein was confirmed in the HEK293T cell.

Example 3. Exosome Separation and Purification

From the medium of the HEK293T cell overexpressing the fusion protein in Example 2 above, the exosome was separated and purified by Tangential Fluid Filtration system.

Figure 5:
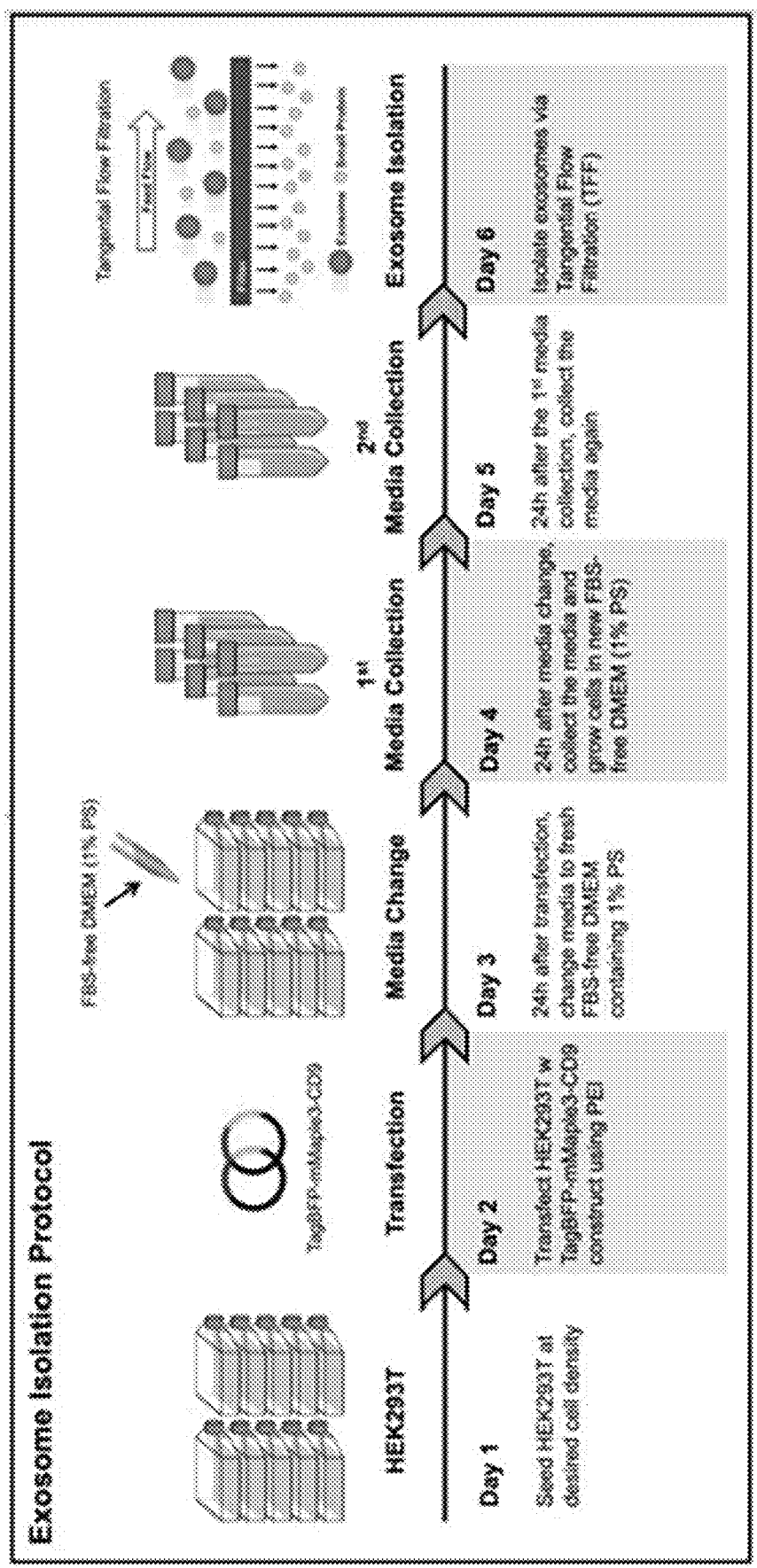
FIG. 5 schematically shows the separation and purification process of the exosome according to one embodiment of the present disclosure.

Specifically, 24 hours after seeding the HEK293T cell, the TagBFP-mMaple3-CD9 cDNA was transfected by using PEI, and 24 hours after transfection, the cell culture medium was replaced with FBS-free DMEM (1% PS (penicillin/streptomycin)) medium. 24 hours after replacing the medium, the medium was collected primarily, and the FBS-free DMEM (1% PS) medium was added again, and after 24 hours, the medium was secondarily collected. The exosome was separated and purified from the medium collected primarily and secondarily by TFF (tangential flow filtration) method. The process of the separation and purification of the exosome was schematically shown in FIG. 5.

After separating and purifying the exosome by the method, the concentration and size of the exosome containing the fusion protein were measured by NTA (Nanoparticle Tracking Assay), DLS (Dynamic Light Scattering) and microBCA (Bicinchoninic Acid Assay).

Figure 6A:
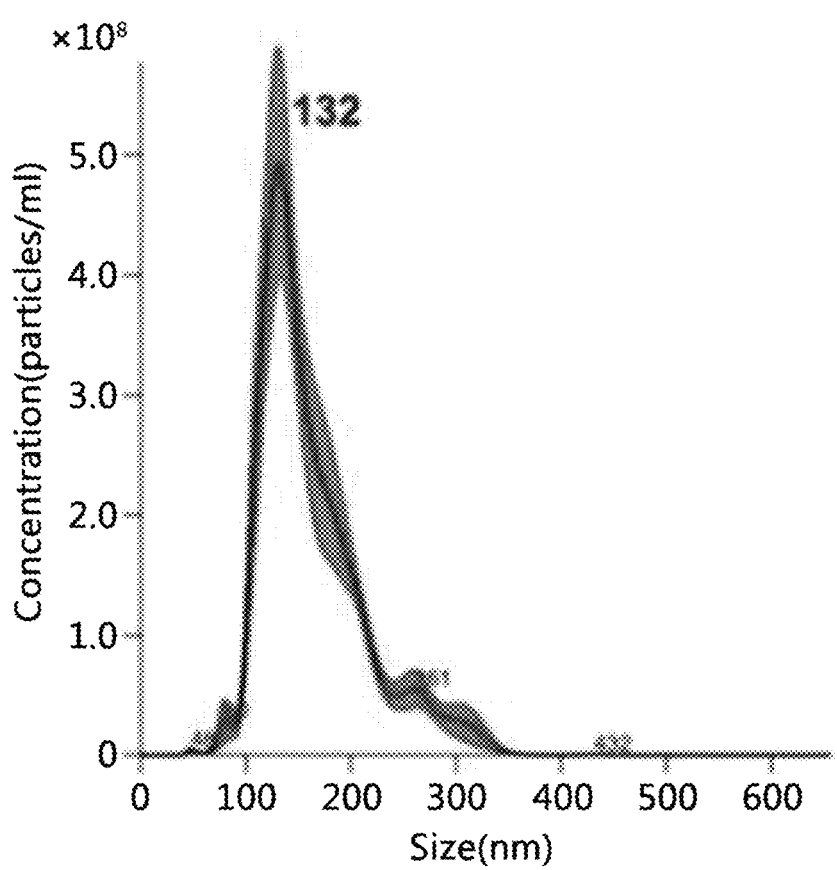
FIG. 6a is the result of measuring the size of the exosome containing the fusion protein (TagBFP-mMaple3-CD9) according to one embodiment of the present disclosure by NTA.
Figure 6B:
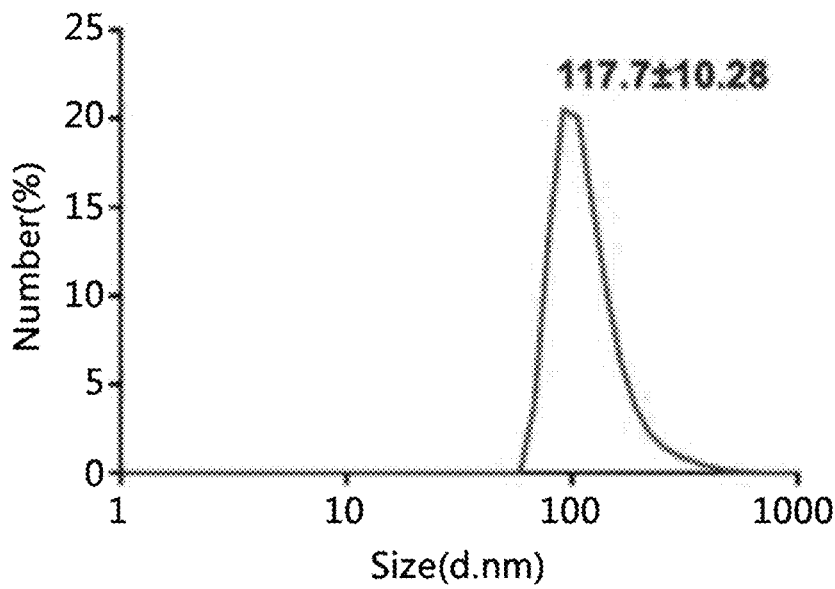
FIG. 6b is the result of measuring the size of the exosome containing the fusion protein (TagBFP-mMaple3-CD9) according to one embodiment of the present disclosure by DLS.

As the result of NTA measurement, as shown in FIG. 6a, the average diameter of the exosome was shown as 132 nm, and as the result of DLS measurement, as shown in FIG. 6b, the average diameter of the exosome was confirmed as 117.7±10.28 nm, and as the result of microBCA measurement, as shown in FIG. 6c, the concentration of the protein of the exosome containing the fusion protein was shown as 1487 mg/mL, and it was confirmed that the amount of the protein contained in one exosome was 39.13 ng.

Furthermore, as the result of measuring a zeta potential of the exosome, as shown in FIG. 6d, it was confirmed as −19.3±0.8 mV on the average, and cryogenic electron microscopy (Cryo-TEM) image observation data of the exosome were shown in FIG. 6e (scale bar: 100 nm)

Figure 6F:
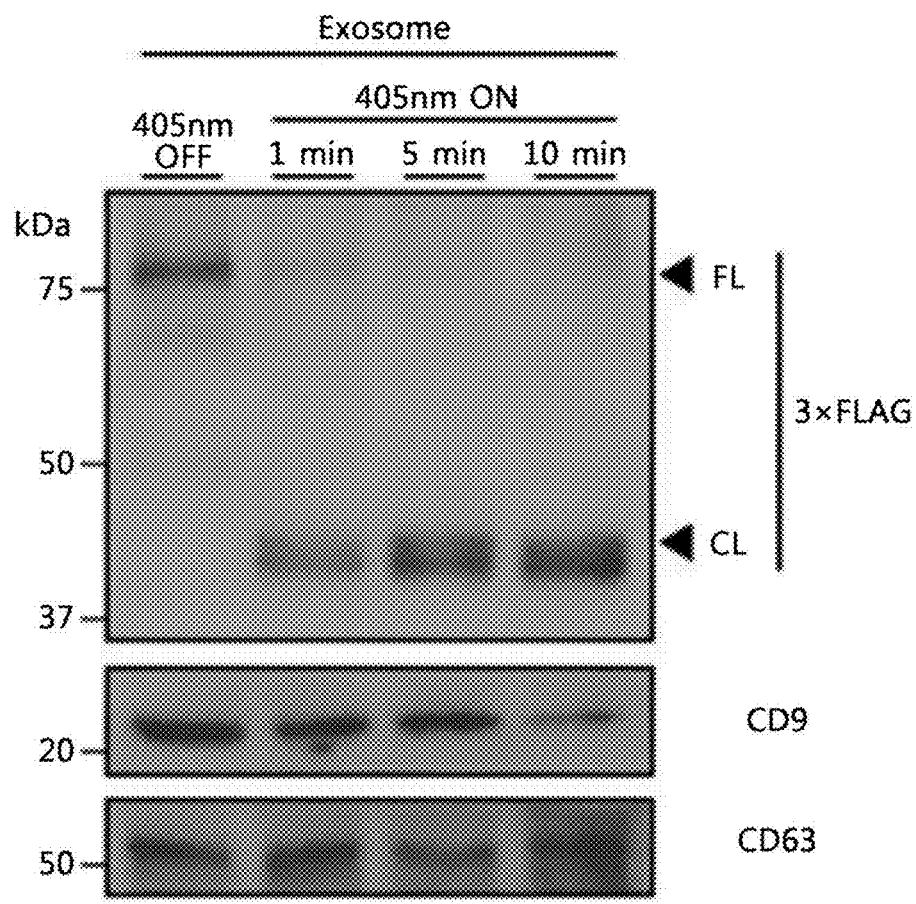
FIG. 6f is the result of confirming the cleavage effect by light irradiation of the fusion protein (TagBFP-mMaple3-CD9) in the exosome according to one embodiment of the present disclosure by western blot.

In addition, as the result of confirming the effect of cleavage of the fusion protein by light of 405 nm in the exosome by western blot, as shown in FIG. 6f, by observing that the amount of the fusion protein not cleaved was reduced over time after irradiating light of 405 nm, whereas the amount of the cleaved fusion protein section was increased, the effect of cleavage of the mMaple3 protein was confirmed in the exosome.

Figure 6G:
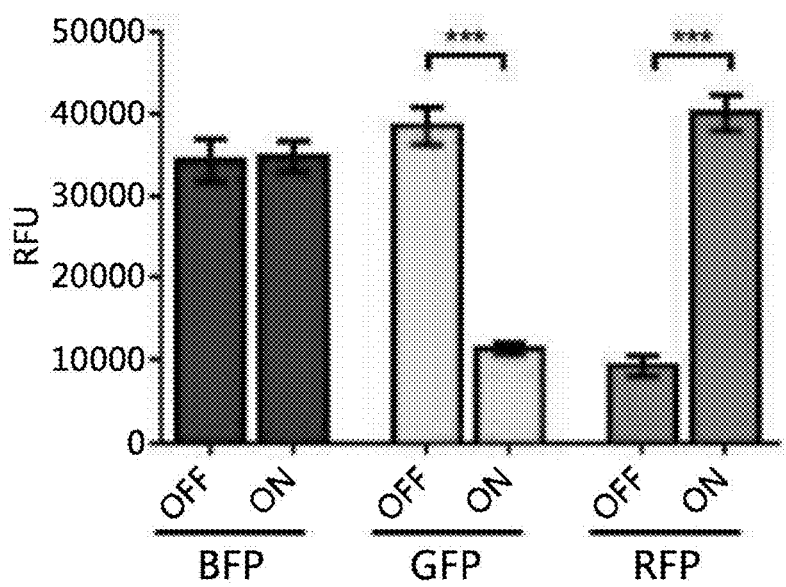
FIG. 6g is the result of confirming the cleavage effect by light irradiation of the fusion protein (TagBFP-mMaple3-CD9) in the exosome according to one embodiment of the present disclosure and whether the blue fluorescent protein is contained in the exosome by fluorescence intensity measurement.

As the result of measuring the intensity of blue fluorescence, green fluorescence and red fluorescence by BioTek microplate reader machine in order to confirm the effect of cleavage of the fusion protein by light of 405 nm and whether the blue fluorescent protein was contained in the exosome once more, as shown in FIG. 6g, it was confirmed that the intensity of blue fluorescence had no difference before and after irradiating light of 405 nm, and it was observed that the intensity of green fluorescence was greatly reduced after irradiating light of 405 nm, whereas the intensity of red fluorescence was increased, and thereby, the effect of cleavage of the fusion protein in the exosome and whether the blue fluorescent protein was contained in the exosome were confirmed.

Example 4. Confirmation of Position of Target Protein in Exosome

In order to confirm the position of the target protein (TagBFP) in the exosome (+mMaple3 exosomes) containing the fusion protein (TagBFP-mMaple3-CD9), separated in Example 3 above, protease digestion assay was performed.

Specifically, degradation of the target protein according to treatment of Triton X-100 and proteinase (proteinase k) which enable permeation of lipid bilayers of the exosome was confirmed.

Figure 7:
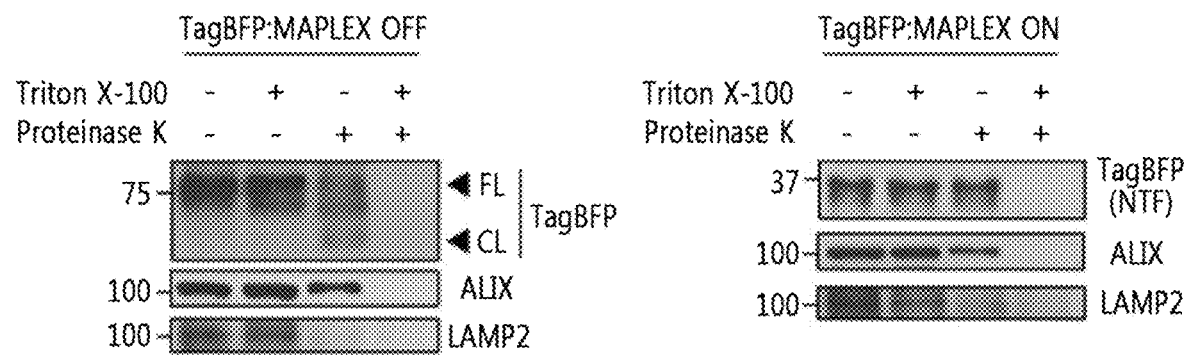
FIG. 7 is the result of confirming whether the target protein is decomposed according to presence or absence of treatment of Triton X-100, proteinase (proteinase K), and light, to the exosome containing the fusion protein (TagBFP-mMaple3-CD9) according to one embodiment of the present disclosure.

As a result, as shown in FIG. 7, it could be found that unless the lipid bilayers of the exosome was artificially permeated by using Triton X-100, the protein (ALIX) present inside the exosome including the target protein (TagBFP) was not degraded and was well protected from the proteinase (proteinase k). On the other hand, it was confirmed that the protein (LAMP2) having a domain outside the exosome was degraded by the proteinase regardless of whether Triton X-100 was treated. In addition, it was confirmed that light of 405 nm did not affect the lipid bilayers of this exosome.

Experimental Example 1. Confirmation of Protein in Exosome into Cell

To the exosome containing the fusion protein (TagBFP-mMaple3-CD9), separated in Example 3 above (+mMaple3 exosomes), and the exosome not containing a specific protein separated and purified from the HEK293T cell culture solution (+Negative exosomes) as a control group, light of 405 nm was treated and they were treated to the HEK293T cell.

Specifically, in 24 hours after seeding the HEK293T cell, the exosome containing the TagBFP-mMaple3-CD9 fusion protein was treated at a concentration of $5 \times 10^9$ particles/mL, and in 24 hours after treating the exosome, the HEK293T cell was fixed with 4% paraformaldehyde and then delivery of the blue fluorescent protein was confirmed with cytation 5 cell imaging machine.

Figure 8A:
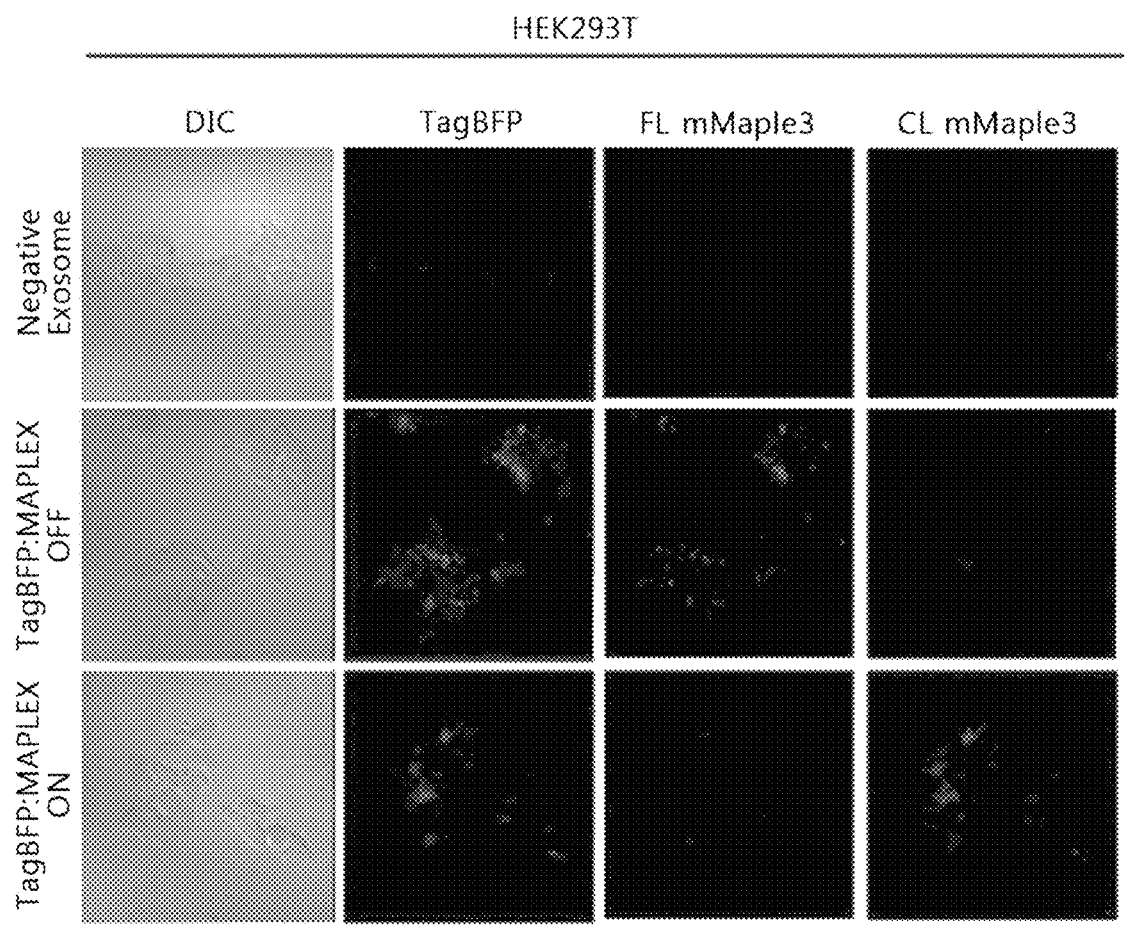
FIGS. 8a and 8b are results of confirming the effect of delivery into a cell of the blue fluorescent protein in the exosome according to one embodiment of the present disclosure.

As a result, as shown in FIG. 8a, it was observed that blue fluorescence (TagBFP) was shown in the cell when the exosome containing mMaple3 was treated, and it was confirmed that green fluorescence (FL mMaple3) was reduced and red fluorescence (CL mMaple3) was increased as light was treated to the exosome.

Figure 8B:
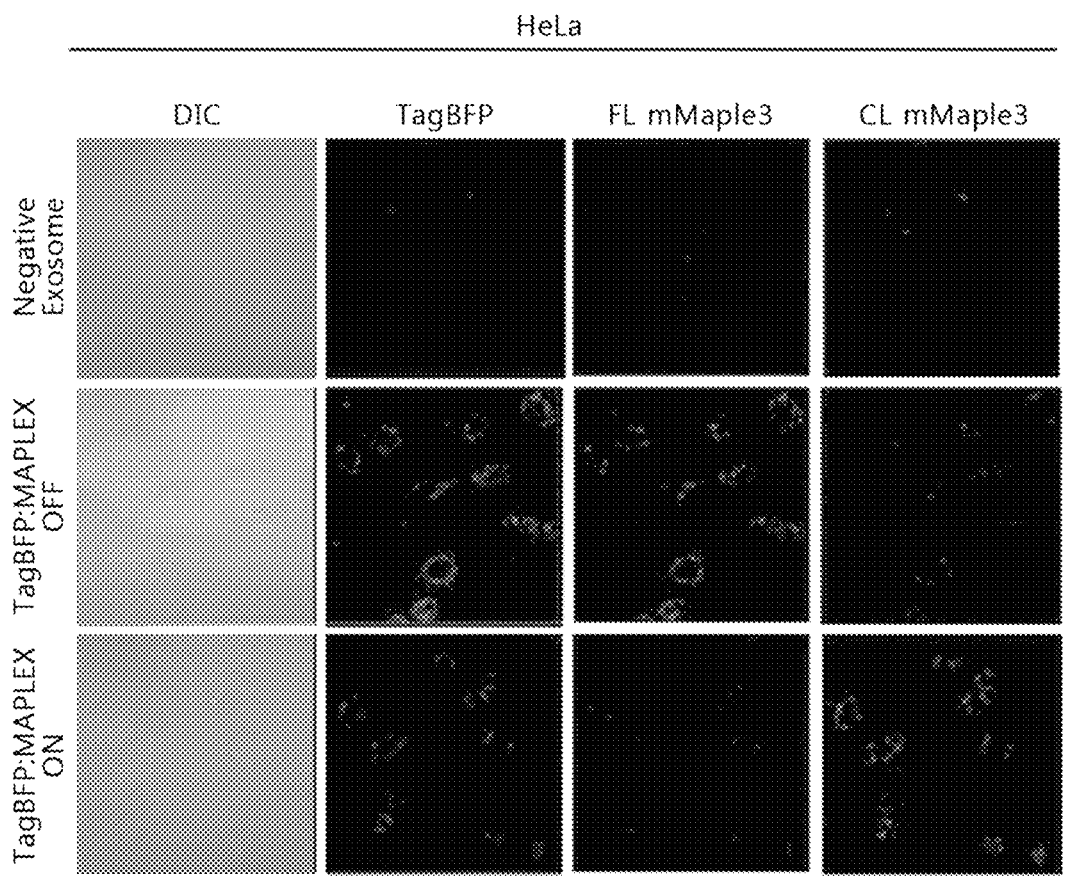

In addition, as the result of confirming delivery of the blue fluorescent protein in the cell after treating the exosome to the HeLa cell by the same method, as shown in FIG. 8b, it was confirmed that blue fluorescence was also shown in the HeLa cell, and it was confirmed that green fluorescence was reduced and red fluorescence was increased when light was treated to the exosome.

From this, it could be confirmed that mMaple3 was cleaved by treatment of 405 nm light in the exosome containing TagBFP-mMaple3-CD9, and thereby, the blue fluorescent protein (TagBFP) was delivered into a cell.

Experimental Example 2. Confirmation of Delivery of Protein in Exosome into Animal Organ Light of 405 nm was treated to the exosome containing the Cre fusion protein (Cre-mMaple3-CD9), separated by the method as Example 3 above, and when the Cre protein was delivered, it was administered into a genetically modified mouse in which the red fluorescent protein (tdTomato) was expressed.

Specifically, the exosome in which phosphate buffer saline (PBS) or light was treated into the genetically modified mouse (Cre: MAPLEX) 500 μg was administered into a tail vein, and then after 1, 6 and 24 hours, the intensity of red fluorescence was measured with IVIS small animal imaging machine.

Figure 9:
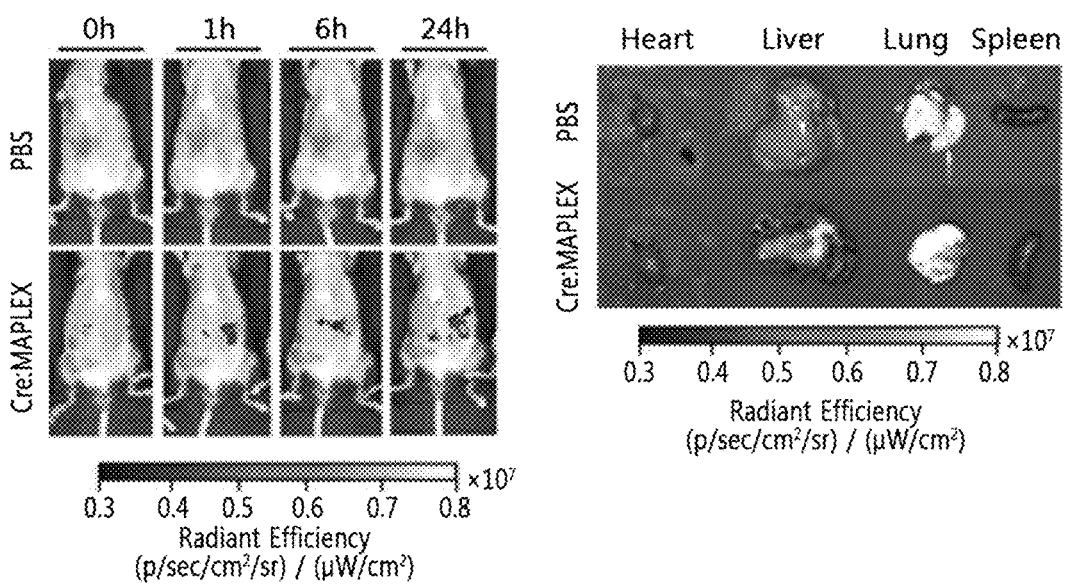
FIG. 9 is the result of confirming the effect of delivery in an animal organ of Cre protein in the exosome when the exosome contains the fusion protein (Cre-mMaple3-CD9) according to one embodiment of the present disclosure into an animal.

As a result, as shown in FIG. 9, it was confirmed that the intensity of red fluorescence was increased in the liver of the mouse in which the light-treated exosome was administered as shown in FIG. 9. From this, it could be confirmed that mMaple3 was cleaved by treatment of 405 nm light in the exosome containing Cre-mMaple3-CD9, and thereby, the Cre protein was effectively delivered into an organ.

The description of the present disclosure described above is for illustration, and those skilled in the art to which the present disclosure pertains can understand that it can be easily modified into other specific forms without changing the technical spirit or essential features of the present disclosure. Therefore, it should be understood that the examples described above are illustrative and not restrictive in all respects.

INDUSTRIAL APPLICABILITY

The exosome containing a photocleavable protein according to the present disclosure is expected to be usefully used in the protein treatment field by safely and efficiently delivering various therapeutic proteins into cells.

The invention claimed is:

1. An exosome comprising a fusion protein which comprises a target protein and mMaple3, wherein the mMaple3 comprises the amino acid sequence as set forth in SEQ ID NO: 1.

2. The exosome according to claim 1,
wherein the mMaple3 is encoded by a gene comprising the nucleotides of as set forth in SEQ ID NO: 2.

3. The exosome according to claim 1,
wherein the fusion protein further comprises an exosome-specific marker.

4. The exosome according to claim 1,
wherein the target protein is to be delivered into a cell.

5. The exosome according to claim 4,
wherein the target protein is for treating a disease or for diagnosing a disease.

6. The exosome according to claim 3,
wherein the exosome-specific marker is one or more selected from the group consisting of CD9, CD63 and CD81.

7. A composition for delivery of a target protein into a cell, comprising the exosome according to claim 1 as an active ingredient.

8. The composition according to claim 7,
wherein the target protein is to be delivered into a cell.

9. The composition according to claim 8,
wherein the target protein is for treating a disease or for diagnosing a disease.

10. A method of delivering a target protein into a cell, comprising:
administering a composition comprising an exosome into a subject in need thereof,
wherein the exosome comprises a fusion protein comprising a target protein and mMaple3.

* * * * *

SEQUENCE LISTING

<160> NUMBER OF SEQ ID NOS: 12

<210> SEQ ID NO 1
<211> LENGTH: 237
<212> TYPE: PRT
<213> ORGANISM: Artificial Sequence
<220> FEATURE:
<223> OTHER INFORMATION: mMaple3

<400> SEQUENCE: 1

```
Met Val Ser Lys Gly Glu Glu Thr Ile Met Ser Val Ile Lys Pro Asp
1               5                   10                  15

Met Lys Ile Lys Leu Arg Met Glu Gly Asn Val Asn Gly His Ala Phe
            20                  25                  30

Val Ile Glu Gly Glu Gly Ser Gly Lys Pro Phe Glu Gly Ile Gln Thr
        35                  40                  45

Ile Asp Leu Glu Val Lys Glu Gly Ala Pro Leu Pro Phe Ala Tyr Asp
50                  55                  60

Ile Leu Thr Thr Ala Phe His Tyr Gly Asn Arg Val Phe Thr Lys Tyr
65                  70                  75                  80

Pro Arg Lys Ile Pro Asp Tyr Phe Lys Gln Ser Phe Pro Glu Gly Tyr
                85                  90                  95

Ser Trp Glu Arg Ser Met Thr Tyr Glu Asp Gly Gly Ile Cys Asn Ala
            100                 105                 110

Thr Asn Asp Ile Thr Met Glu Glu Asp Ser Phe Ile Asn Lys Ile His
        115                 120                 125

Phe Lys Gly Thr Asn Phe Pro Pro Asn Gly Pro Val Met Gln Lys Arg
130                 135                 140

Thr Val Gly Trp Glu Val Ser Thr Glu Lys Met Tyr Val Arg Asp Gly
145                 150                 155                 160

Val Leu Lys Gly Asp Val Lys Met Lys Leu Leu Leu Lys Gly Gly Ser
                165                 170                 175

His Tyr Arg Cys Asp Phe Arg Thr Thr Tyr Lys Val Lys Gln Lys Ala
            180                 185                 190

Val Lys Leu Pro Lys Ala His Phe Val Asp His Arg Ile Glu Ile Leu
        195                 200                 205

Ser His Asp Lys Asp Tyr Asn Lys Val Lys Leu Tyr Glu His Ala Val
210                 215                 220

Ala Arg Asn Ser Thr Asp Ser Met Asp Glu Leu Tyr Lys
225                 230                 235
```

<210> SEQ ID NO 2
<211> LENGTH: 711
<212> TYPE: DNA
<213> ORGANISM: Artificial Sequence
<220> FEATURE:
<223> OTHER INFORMATION: mMaple3

<400> SEQUENCE: 2

```
atggtgagca aggcgagga  gacaatcatg tccgtgatca agcccgacat gaagatcaaa    60
ctgaggatgg agggcaacgt gaacggccac gccttcgtga tcgagggcga aggaagcggc   120
aagcccttcg agggcatcca gaccatcgat ctggaggtca aggagggcgc tcccctccct   180
ttcgcctatg acatcctgac caccgccttc cactacggca taggggtgtt caccaagtat   240
cccaggaaga tccccgacta cttcaagcag agcttccctg agggctacag ctgggagagg   300
agcatgacat acgaggacgg cggcatctgc aacgccacca acgacatcac aatggaggag   360
```

```
gacagcttca tcaacaagat ccacttcaaa ggcacaaact tccccccaa tggccccgtg      420 atgcagaaga ggaccgtggg ctgggaggtg agcaccgaga agatgtacgt gagggacggc      480
gtcctgaagg gcgacgtgaa gatgaagctc ctgctcaagg gcggcagcca ctacaggtgc      540
gactttagga ccacctataa ggtgaagcag aaggctgtga agctgcccaa ggcccacttc      600
gtcgaccata ggatcgagat cctgtcccac gacaaggact acaacaaggt caagctgtac      660
gagcacgccg tcgctaggaa cagcaccgac agcatggacg aactctataa g            711
```

<210> SEQ ID NO 3
<211> LENGTH: 228
<212> TYPE: PRT
<213> ORGANISM: Artificial Sequence
<220> FEATURE:
<223> OTHER INFORMATION: CD9

<400> SEQUENCE: 3

```
Met Pro Val Lys Gly Gly Thr Lys Cys Ile Lys Tyr Leu Leu Phe Gly
1               5                   10                  15

Phe Asn Phe Ile Phe Trp Leu Ala Gly Ile Ala Val Leu Ala Ile Gly
            20                  25                  30

Leu Trp Leu Arg Phe Asp Ser Gln Thr Lys Ser Ile Phe Glu Gln Glu
        35                  40                  45

Thr Asn Asn Asn Ser Ser Phe Tyr Thr Gly Val Tyr Ile Leu Ile
    50                  55                  60

Gly Ala Gly Ala Leu Met Met Leu Val Gly Phe Leu Gly Cys Cys Gly
65                  70                  75                  80

Ala Val Gln Glu Ser Gln Cys Met Leu Gly Leu Phe Phe Gly Phe Leu
                85                  90                  95

Leu Val Ile Phe Ala Ile Glu Ile Ala Ala Ala Ile Trp Gly Tyr Ser
            100                 105                 110

His Lys Asp Glu Val Ile Lys Glu Val Gln Glu Phe Tyr Lys Asp Thr
        115                 120                 125

Tyr Asn Lys Leu Lys Thr Lys Asp Glu Pro Gln Arg Glu Thr Leu Lys
    130                 135                 140

Ala Ile His Tyr Ala Leu Asn Cys Cys Gly Leu Ala Gly Gly Val Glu
145                 150                 155                 160

Gln Phe Ile Ser Asp Ile Cys Pro Lys Lys Asp Val Leu Glu Thr Phe
                165                 170                 175

Thr Val Lys Ser Cys Pro Asp Ala Ile Lys Glu Val Phe Asp Asn Lys
            180                 185                 190

Phe His Ile Ile Gly Ala Val Gly Ile Gly Ile Ala Val Val Met Ile
        195                 200                 205

Phe Gly Met Ile Phe Ser Met Ile Leu Cys Cys Ala Ile Arg Arg Asn
    210                 215                 220

Arg Glu Met Val
225
```

<210> SEQ ID NO 4
<211> LENGTH: 684
<212> TYPE: DNA
<213> ORGANISM: Artificial Sequence
<220> FEATURE:
<223> OTHER INFORMATION: CD9

<400> SEQUENCE: 4

```
atgccggtca aaggaggcac caagtgcatc aaatacctgc tgttcggatt aacttcatc       60
```

```
ttctggcttg ccgggattgc tgtccttgcc attggactat ggctccgatt cgactctcag    120
accaagagca tcttcgagca agaaactaat aataataatt ccagcttcta cacaggagtc    180
tatattctga tcggagccgg cgccctcatg atgctggtgg gcttcctggg ctgctgcggg    240
gctgtgcagg agtcccagtg catgctggga ctgttcttcg gcttcctctt ggtgatattc    300
gccattgaaa tagctgcggc catctgggga tattcccaca aggatgaggt gattaaggaa    360
gtccaggagt tttacaagga cacctacaac aagctgaaaa ccaaggatga gcccagcgg    420 gaaacgctga aagccatcca ctatgcgttg aactgctgtg gtttggctgg gggcgtggaa    480
cagtttatct cagacatctg ccccaagaag gacgtactcg aaaccttcac cgtgaagtcc    540
tgtcctgatg ccatcaaaga ggtcttcgac aataaattcc acatcatcgg cgcagtgggc    600
atcggcattg ccgtggtcat gatatttggc atgatcttca gtatgatctt gtgctgtgct    660
atccgcagga accgcgagat ggtc                                           684
```

```
<210> SEQ ID NO 5
<211> LENGTH: 233
<212> TYPE: PRT
<213> ORGANISM: Artificial Sequence
<220> FEATURE:
<223> OTHER INFORMATION: TagBFP

<400> SEQUENCE: 5
```

Met Ser Glu Leu Ile Lys Glu Asn Met His Met Lys Leu Tyr Met Glu
1               5                   10                  15

Gly Thr Val Asp Asn His His Phe Lys Cys Thr Ser Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Leu Tyr
    50                  55                  60

Gly Ser Lys Thr Phe Ile Asn His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Cys Leu Ile Tyr Asn Val Lys Ile Arg Gly Val Asn Phe Thr Ser
        115                 120                 125

Asn Gly Pro Val Met Gln Lys Lys Thr Leu Gly Trp Glu Ala Phe Thr
    130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala Asn Ile Lys Thr
                165                 170                 175

Thr Tyr Arg Ser Lys Lys Pro Ala Lys Asn Leu Lys Met Pro Gly Val
            180                 185                 190

Tyr Tyr Val Asp Tyr Arg Leu Glu Arg Ile Lys Glu Ala Asn Asn Glu
        195                 200                 205

Thr Tyr Val Glu Gln His Glu Val Ala Val Ala Arg Tyr Cys Asp Leu
    210                 215                 220

Pro Ser Lys Leu Gly His Lys Leu Asn
225                 230

```
<210> SEQ ID NO 6
```

```
<211> LENGTH: 699
<212> TYPE: DNA
<213> ORGANISM: Artificial Sequence
<220> FEATURE:
<223> OTHER INFORMATION: TagBFP

<400> SEQUENCE: 6
atgagcgagc tgattaagga gaacatgcac atgaagctgt acatggaggg caccgtggac      60
aaccatcact tcaagtgcac atccgagggc gaaggcaagc cctacgaggg cacccagacc     120
atgagaatca aggtggtcga gggcggccct ctccccttcg ccttcgacat cctggctact     180
agcttcctct acggcagcaa gaccttcatc aaccacaccc agggcatccc cgacttcttc     240
aagcagtcct tccctgaggg cttcacatgg gagagagtca ccacatacga agacgggggc     300
gtgctgaccg ctacccagga caccagcctc caggacggct gcctcatcta caacgtcaag     360
atcagagggg tgaacttcac atccaacggc cctgtgatgc agaagaaaac actcggctgg     420
gaggccttca ccgagacgct gtaccccgct gacggcggcc tggaaggcag aaacgacatg     480
gccctgaagc tcgtgggcgg gagccatctg atcgcaaaca tcaagaccac atatagatcc     540
aagaaacccg ctaagaacct caagatgcct ggcgtctact atgtggacta cagactggaa     600
agaatcaagg aggccaacaa cgagacctac gtcgagcagc acgaggtggc agtggccaga     660
tactgcgacc tccctagcaa actggggcac aagcttaat                            699

<210> SEQ ID NO 7
<211> LENGTH: 27
<212> TYPE: DNA
<213> ORGANISM: Artificial Sequence
<220> FEATURE:
<223> OTHER INFORMATION: TagBFP-Linker forward primer

<400> SEQUENCE: 7
tatgctgaat tcgccaccat gagcgag                                          27

<210> SEQ ID NO 8
<211> LENGTH: 52
<212> TYPE: DNA
<213> ORGANISM: Artificial Sequence
<220> FEATURE:
<223> OTHER INFORMATION: TagBFP-Linker reverse primer

<400> SEQUENCE: 8
ggaagcttga gctcgagatc tgagtccgga attaagcttg tgccccagtt tg              52

<210> SEQ ID NO 9
<211> LENGTH: 36
<212> TYPE: DNA
<213> ORGANISM: Artificial Sequence
<220> FEATURE:
<223> OTHER INFORMATION: Linker-mMaple3-Linker forward primer

<400> SEQUENCE: 9
tctcgagctc aagcttccgt gagcaaaggc gaggag                                36

<210> SEQ ID NO 10
<211> LENGTH: 51
<212> TYPE: DNA
<213> ORGANISM: Artificial Sequence
<220> FEATURE:
<223> OTHER INFORMATION: Linker-mMaple3-Linker reverse primer

<400> SEQUENCE: 10
acctccgcct gaaccgccac ctcccgactt atagagttcg tccatgctgt c               51
```

```
<210> SEQ ID NO 11
<211> LENGTH: 56
<212> TYPE: DNA
<213> ORGANISM: Artificial Sequence
<220> FEATURE:
<223> OTHER INFORMATION: Linker-CD9 forward primer

<400> SEQUENCE: 11
ggcggttcag gcggaggtgg ctctggcggt ggcggatcgc cggtcaaagg aggcac         56

<210> SEQ ID NO 12
<211> LENGTH: 31
<212> TYPE: DNA
<213> ORGANISM: Artificial Sequence
<220> FEATURE:
<223> OTHER INFORMATION: Linker-CD9 reverse primer

<400> SEQUENCE: 12
ccctctagtc tagagaccat ctcgcggttc c                                    31
```